United States Patent [19]

Miyata

[11] Patent Number: 5,344,636
[45] Date of Patent: Sep. 6, 1994

[54] ANTI-MICROORGANISM AGENT AND ANTI-MICROORGANISM RESIN OR RUBBER COMPOSITION

[75] Inventor: Shigeo Miyata, Takamatsu, Japan

[73] Assignee: Kabushiki Kaisha Kaisui Kagaku Kenkyujo, Kagawa, Japan

[21] Appl. No.: 979,230

[22] Filed: Nov. 20, 1992

[30] Foreign Application Priority Data

Nov. 27, 1991 [JP] Japan ................................. 3-337594
Aug. 24, 1992 [JP] Japan ................................. 4-247420

[51] Int. Cl.$^5$ .......................... C01F 5/14; A61K 33/06; A61K 33/34; C08K 3/22
[52] U.S. Cl. .................... 423/593; 424/633; 424/635; 424/641; 424/688; 424/692; 424/693; 524/431; 524/432; 524/433; 524/436
[58] Field of Search ............. 524/431, 432, 433, 436; 423/593; 424/633, 635, 641, 692, 693, 688

[56] References Cited

U.S. PATENT DOCUMENTS 3,231,464  1/1966  Dettwiller et al. ................. 424/692
3,607,409  9/1971  Hamlen et al. ..................... 423/593

FOREIGN PATENT DOCUMENTS 0488566  8/1992  European Pat. Off. .

OTHER PUBLICATIONS

Grant & Hackh's Chemical Dictionary, Fifth Edition, McGraw–Hill Book Company, 1987, p. 640.
Kurmanguzhina et al., Chemical Abstracts, vol. 115, No. 18 Nov. 4, 1991 Abstract No. 186227oa.
Traore, Chemical Abstracts, vol. 81, No. 14, Oct. 7, 1974 Abstract No. 85321a.
Hokko Kagaku Kogyo KK, Patent Abstracts of Japan Abstracting JP 57112311 Jul. 13, 1982.

*Primary Examiner*—Peter Szekely
*Attorney, Agent, or Firm*—Wenderoth, Lind & Ponack

[57] ABSTRACT

A anti-microorganism agent completely or nearly free of toxicity, insoluble or sparingly soluble in water or an organic solvent so as not to contaminate the environment and highly effective as such, which is composed of at least one of a composite metal hydroxide of the formula (1), $$(M_1^{2+})_{1-x}(M_2^{2+})_x(OH)_2 \qquad (1)$$

wherein $M_1^{2+}$ is at least one of $Mg^{2+}$ and $Ca^{2+}$, $M_2^{2+}$ is at least one of $Cu^{2+}$ and $Zn^{2+}$, and x is defined by $0.001 \leq x < 0.9$, and a composite metal oxide of the formula (2), $$(M_1^{2+})_{1-y}(M_2^{2+})_y O \qquad (2)$$

wherein $M_1^{2+}$ is at least one of $Mg^{2+}$ and $Ca^{2+}$, $M_2^{2+}$ is at least one of $Cu^{2+}$ and $Zn^{2+}$, and y is defined by $0.001 \leq y \leq 0.5$, and an anti-microorganism resin or rubber composition containing said anti-microorganism agent.

3 Claims, No Drawings

ANTI-MICROORGANISM AGENT AND ANTI-MICROORGANISM RESIN OR RUBBER COMPOSITION

FIELD OF THE INVENTION

The present invention relates to a novel anti-microorganism agent and an anti-microorganism resin or rubber composition, More specifically, it relates to an anti-microorganism agent which itself has no toxicity or very low toxicity, which has excellent dispersibility in resins, rubbers and coating compositions, and which improves the thermal stability of resins, rubbers and coating compositions when incorporated thereto, specifically an antibacterial agent and an anti-mold agent, and an anti-microorganism resin or rubber composition containing said anti-microorganism agent.

PRIOR ART

A climate in regions having relatively high temperatures and high humidities, e.g., in Japan, is suitable for propagation of microorganisms. Due to this, microorganisms (bacteria) may occur in drinking water or foods in some cases to seriously affect human lives. Further, in some cases, microorganisms (mold) may occur on foods, cosmetics, plastic products, wallpaper, inner and outer fittings of an automobile, construction materials, electric cables, cables, synthetic leather, sealants, rubber hoses, adhesives, roofings, floor materials, woods, coating compositions, etc., to cause discoloration, odor or deterioration in strength. For example, mold occurring on an electric cable may result in electric leakage, and there is a risk that fire may break out or that an electric shock or electrocution may be caused, Further, microorganisms may damage valuable cultural assets, mold occurring on plastics may cause cancer or allergic pneumonia, many ticks may occur due to propagated bacteria as feed, and parasitic trichophyton may cause athlete's foot and eczema marginatum.

In recent years, it has been increasingly desired to prevent such microorganisms-induced disasters and diseases as above, and a variety of anti-microorganism agents are commercially available. These anti-microorganism agents are classified into halogen compounds containing chlorine, bromine and iodine; inorganic compounds such as glass containing copper arsenite, cuprous oxide, silver nitrate, silver and copper; nitrogen compounds such as amines and triazine; organic metal compounds containing arsenic, copper, mercury, tin and zinc; organic sulfur compounds such as isothiazolone, pyrithione and thiocyanate; quaternary ammonium compounds such as an alkyldimethylbenzylammonium compound; and phenolic compounds such as chlorinated phenol, bisphenol and o-phenylphenol.

Greater importance recently tends to be attached to safety and influence on environments, and this tendency is considered to grow. However, many existing anti-microorganism agents have high toxicity, and they are mostly water-soluble or liable to contaminate the environment. Further, they are expensive for their effects.

Furthermore, many existing anti-microorganism agents degrade heat resistance and weatherability of products, and cause decomposition and foaming of resins and rubbers at temperatures for processing the resins and rubbers. Due to their coarse particles, in many cases, such anti-microorganism agents show poor dispersibility in coating compositions, and a product formed of a resin or rubber containing such an anti-microorganism agent has a poor appearance and a decreased mechanical strength.

SUMMARY OF THE INVENTION

It is an object of the present invention to provide a novel anti-microorganism agent which is completely or nearly free of toxicity, which is insoluble or sparingly soluble in water or an organic solvent so as not to contaminate the environment and which has a high anti-microorganism effect, and an anti-microorganism resin or rubber composition containing said anti-microorganism agent.

It is another object of the present invention to prove an anti-microorganism agent which itself is stable to heat and ultraviolet light, which is excellent in properties such as moldability, molded article appearance and mechanical strength due to its excellent dispersibility in resins, rubbers and coating compositions, and which, unlike an existing copper- or zinc-containing anti-microorganism agent, does not much impair the thermal stability of halogen-containing resins such as a vinyl chloride resin, and an anti-microorganism resin or rubber composition containing said anti-microorganism agent.

According to the present invention, there is provided an anti-microorganism agent composed of at least one of a composite metal hydroxide of the formula (1), $$(M_1^{2+})_{1-x}(M_2^{2+})_x(OH)_2 \qquad (1)$$

wherein $M_1^{2+}$ is at least one of $Mg^{2+}$ and $Ca^{2+}$, $M_2^{2+}$ is at least one of $Cu^{2+}$ and $Zn^{2+}$, and x is defined by $0.001 \leq x < 0.9$, preferably by $0.001 \leq x \leq 0.4$, more preferably by $0.01 \leq x \leq 0.2$, and a composite metal oxide of the formula (2), $$(M_1^{2+})_{1-y}(M_2^{2+})_y O \qquad (2)$$

wherein $M_1^{2+}$ is at least one of $Mg^{2+}$ and $Ca^{2+}$, $M_2^{2+}$ is at least one of $Cu^{2+}$ and $Zn^{2+}$, and y is defined by $0.001 \leq y \leq 0.5$, preferably by $0.005 \leq y \leq 0.4$, more preferably by $0.01 \leq y \leq 0.3$.

Further, according to the present invention, there is also provided an anti-microorganism resin or rubber composition containing 100 parts by weight of a resin or rubber, and 0.001 to 50 parts by weight, preferably 0.001 to 15 parts by weight, more preferably 0.01 to 5 parts by weight of at least one of the above composite metal hydroxide of the formula (1) and the above composite metal oxide of the formula (2).

DETAILED DESCRIPTION OF THE INVENTION

On the one hand, existing organic anti-microorganism agents cause problems on toxicity, heat resistance and weatherability, and on the other hand, existing inorganic compounds only produce low effects as anti-microorganism agents and impair the properties of resins and rubbers. Therefore, the present inventor has focused on copper ion and zinc ion which are completely or nearly free of toxicity are inexpensive. However, existing anti-microorganism agents containing these show poor anti-microorganism effects. Further, the present inventor has made a diligent study on why inorganic anti-microorganism agents containing these cause the above problems. As a result, the present inventor has arrived at a conclusion that these anti-microorganism agents have poor solubility in water, i.e., are sparingly soluble, which causes the above problems.

That is, the conclusion is that the concentration of the copper ion or zinc ion as an active component hardly increases to such an extent that the effect as an anti-microorganism agent can be fully produced, since the above anti-microorganism agents are sparingly soluble, and that existing anti-microorganism agents such as cuprous oxide and zinc oxide deteriorate the heat resistance and weatherability of resins and rubbers, since these are solid acids.

The present inventor has therefore made a diligent study to overcome all of the above problems of anti-microorganism agents of inorganic compounds, and as a result, has arrived at the present invention of an anti-microorganism agent composed of the composite metal hydroxide of the formula (1) as an active component and an anti-microorganism resin or rubber composition containing said anti-microorganism agent. The composite metal hydroxide of the formula (1) has a hexagonal plate-like or fibrous crystal form. That is, the present inventor has found that when a solid solution of $Cu^{2+}$ and/or $Zn^{2+}$ as an active ingredient in $Ca(OH)_2$ and/or $Mg(OH)_2$ is formed, $Cu^{2+}$ and/or $Zn^{2+}$ can be eluted at a solubility level close to the solubility of $Ca(OH)_2$ or $Mg(OH)_2$ in water, i.e., at a level between a slightly-soluble level to a slightly-sparingly-soluble level, and it has been found that due to this, the solid solution shows improved anti-microorganism properties. $Ca(OH)_2$ and $Mg(OH)_2$ are solid bases, and rather work to improve the heat resistance and weatherability of resins and rubbers. Further, the composite metal hydroxide of the present invention has a decomposition initiation temperature of about 300° C. or higher, and does not cause any decomposition and foaming problems at temperatures at which resins and rubbers are processed. The composite metal hydroxide of the formula (1), in which the concentrations of copper ion and zinc ion are maintained at a considerably low level, can exhibit an anti-microorganism effect. Therefore, an anti-microorganism agent containing the composite metal hydroxide of the formula (1) advantageously shows decreased toxicity or no toxicity. The zinc-containing composite metal hydroxide of the formula (1) also has advantages that it is excellent in whiteness or does not color resins or rubbers when incorporated into the resins or rubbers.

The composite metal hydroxide of the formula (1) is a novel compound which the present inventor has produced. The composite metal hydroxide of the formula (1) is a solid solution of $Cu^{2+}$ and/or $Zn^{2+}$ in $Ca(OH)_2$ and/or $Mg(OH)2$, has the same crystal structure as that of $Ca(OH)_2$ or $Mg(OH)_2$, and gives almost the same diffraction pattern as that of $Ca(OH)_2$ or $Mg(OH)_2$, as described in Japanese Patent Publications Nos. 3-36816 and 3-319827.

When the value of "x" in the formula (1) is 0.9 or more, the solid solution of the formula (1) is no longer formed, and the resultant compound hardly shows an anti-microorganism effect. When the value of "x" in the formula (1) exceeds 0.4, undesirably, basic salts and oxides of copper and zinc which do not participate in formation of the solid solution are liable to be formed as byproducts, and the anti-microorganism effect reaches its limit. When the value of "x" is too small, the concentration of released copper ion and/or zinc ion is too low to produce the effects of the present invention. Further, there is an tendency that with an increase in the concentration of copper ion and/or zinc ion in the compound of the formula (1), the releasability of copper ion and/or zinc ion into water decreases and the anti-microorganism effect consequently decreases. Therefore, the value of "x" in the composite metal hydroxide of the formula (1) is limited to $0.001 \leq x < 0.9$, preferably to $0.001 \leq x \leq 0.4$, more preferably to $0.01 \leq x \leq 0.2$. In the present invention, a mixture of the composite metal hydroxide of the formula (1) with basic salts, oxides and hydroxides which are formed as byproducts may be used as an anti-microorganism agent.

A further study by the present inventor has also revealed that the composite metal oxide of the formula (2) obtained by calcining the composite metal hydroxide of the formula (1) exhibits higher activity as an anti-microorganism agent than the composite metal hydroxide of the formula (1). It has been also revealed that the incorporation of the composite metal oxide of the formula (2) into a resin or rubber gives a flame-retardant resin or rubber composition having more improved properties, i.e., more improved heat resistance and weatherability, than a resin or rubber composition into which the composite metal hydroxide of the formula (1) is incorporated. The composite metal oxide of the formula (2) has a variety of crystal forms of scales, spheres and fibers.

Although being not clear, the reason for achievement of the above improved properties is assumed as follows. Copper and/or zinc form(s) a solid solution of copper and/or zinc in magnesium oxide or calcium oxide, and copper and/or zinc in the form of molecules is/are dispersed in the crystal of magnesium oxide or calcium oxide to prevent the crystallization of cupric oxide or zinc oxide. Therefore, the solid solution is very active, and that calcium oxide or magnesium oxide shows proper solubility in water. As a result, the solid solution keeps on releasing copper ion and/or zinc ion for a long period of time. The "proper solubility" means a solubility at which the calcium oxide or magnesium oxide is much more easily dissolved than cupric oxide and zinc oxide but it is not so easily dissolved in water as cupric nitrate and zinc nitrate. Further, magnesium oxide and calcium oxide prevent the deterioration of heat resistance and weatherability of resins and rubbers, particularly halogen-containing resins such as vinyl chloride. Although cupric oxide and zinc oxide, particularly cupric oxide, deteriorate heat resistance and weatherability of resins and rubbers, particularly halogen-containing resins such as vinyl chloride, the composite metal oxide of the present invention rather improves resin and rubbers in heat resistance and weatherability, since magnesium oxide or calcium oxide in the solid solution serves as heat stabilizers and improves these properties sufficiently.

The composite metal oxide of the present invention is pricewise advantageous since it has a composition in which zinc oxide and cupric oxide are dissolved in magnesium oxide and calcium oxide which are less expensive than zinc oxide and cuprio oxide. A zinc-containing compound of the formula (2) is not only free of toxicity but also excellent in whiteness, concealing properties and resistance to ultraviolet light. The zinc-containing compound has an advantage that resins and rubbers to which this compound is incorporated can be freely colored. In a copper-containing compound of the formula (2), the copper color is "diluted" with magnesium oxide and/or calcium oxide. Therefore, the copper-containing compound has an advantage that the degree of coloring resins and rubbers by this compound is remarkably lower than the degree of coloring by a cupric oxide or cuprous oxide compound.

The composite metal oxide of the formula (2) is a novel compound which the present inventor has produced, and can be obtained by calcining a hexagonal plate-like or fibrous composite metal hydroxide disclosed in Japanese Patent Applications Nos. 3-36816, 3-124758, 3-162203 and 3-319827 at a temperature of about 300° C. or higher. The so-obtained compound is a solid solution of copper ion ($Cu^{2+}$) and/or zinc ion ($Zn^{2+}$) in magnesium oxide and/or calcium oxide, and has the same crystal structure as that of magnesium oxide or calcium oxide. When subjected to powder X-ray diffractometry, this compound shows almost the same diffraction pattern as that of magnesium oxide or calcium oxide.

When the value of "y" in the formula (2) exceeds 0.5, cupric oxide and/or zinc oxide are included in the solid solution of the formula (2), and the solid solution of the formula (2) tend to fail to show the above-described advantages. When the value of "y" is less than 0.001, the concentration of copper and/or zinc as active component(s) for producing an anti-microorganism effect is too low to exhibit an excellent anti-microorganism effect. Therefore, the value of "y" in the formula (2) is limited to $0.001 \leq y \leq 0.5$, preferably to $0.005 \leq y \leq 0.4$, more preferably to $0.01 \leq y \leq 0.3$. In the present invention, a mixture of the composite metal oxide of the formula (2) with cupric oxide and/or zinc oxide as by-product(s) may be used as an anti-microorganism agent.

The composite metal hydroxide of the formula (1) can be produced by preparing a mixed aqueous solution of an aqueous solution containing $Ca^{2+}$ and/or $Mg^{2+}$ with an aqueous solution containing $Cu^{2+}$ and/or $Zn^{2+}$, adding an alkaline substance in an amount equal to or less than the total equivalent weight of these cations to the mixed aqueous solution, reacting the resultant mixture with stirring, optionally hydrothermally reacting the reaction mixture in an autoclave at a temperature approximately between 100° C. and 200° C., and then employing proper conventional means for washing, dehydration, drying, milling and classification.

The composite metal oxide of the formula (2) can be produced by calcining the above-obtained composite metal hydroxide at a temperature approximately between 300° C. and 1,200° C., preferably approximately between 400° C. and 900° C., for approximately 0.1 to 10 hours, and employing conventional means for milling, surface-treating and classification.

For improving the anti-microorganism agent of the present invention in the dispersibility in, and affinity to, resins and rubbers, the anti-microorganism agent may be surface-treated with an anionic surfactant, aluminum, a titanate coupling agent, a fatty acid ester of polyhydric alcohol, or the like, according to a conventional method.

The anti-microorganism agent of the present invention can be used in a variety of the fields which may be affected by microorganisms, such as the fields of drinking water, foods, resins, rubbers, wall paper, interior fittings for a bath room, electric cables, floor materials, cement, shower curtains, foaming urethane, buoy ropes, vinyl sheets, agricultural films, synthetic leather, sealants, construction materials, furniture, fiber products such as cloth, a tent, socks and nonwoven fabric, coating compositions for coating the bottom of a ship, adhesives, wood, bamboo materials, cosmetics, products for use in the mouth such as a toothbrush, swimming pools and cooling towers.

The amount of the anti-microorganism agent of the present invention per 100 parts by weight of an intended material (e.g., resins and rubbers) is generally 0.001 to 50 parts by weight, preferably 0.001 to 15 parts by weight, more preferably 0.01 to 5 parts by weight, while this amount is properly selected depending upon use. The average anti-microorganism agent of the present invention can be of fine particles having an average secondary particle diameter of approximately 0.1 to 2 $\mu m$. Even the composite metal hydroxide of the formula (1) is stable up to a processing temperature of about 300° C. When it is incorporated into a fiber material, therefore, it can be fully kneaded with, and dispersed in, the material before, e.g., spinning. The composite metal hydroxide of the formula (1) exhibits excellent dispersibility without being decomposed or foamed at temperatures at which resins and rubbers are treated. Therefore, it does not impair the appearance of a molded article, nor does it impair the mechanical strength of a molded article. Further, the anti-microorganism agent of the present invention is also stable to ultraviolet light.

The composite metal hydroxide of the formula (1) is a solid base, and the activity of this composite metal hydroxide in neutralizing and inactivating acids and halogens is equal to, or higher than, the activity of any one of $Mg(OH)_2$ and $Ca(OH)_2$. Therefore, the composite metal hydroxide of the formula (1) improves resins and rubbers in thermal stability and weatherability.

Although not specially limited, the resin and rubber used in the present invention include thermoplastic resins such as polyethylene, a copolymer of ethylene and other olefin, a copolymer of ethylene and vinyl acetate, ethyl acrylate or methyl acrylate, polypropylene, a copolymer of propylene and other $\alpha$-olefin, polybutene-1, polystyrene, a copolymer of styrene and acrylonitrile, a copolymer of ethylene and propylene diene rubber or butadiene, vinyl acetate, polyacrylate, polymethacrylate, polyurethane, polyester, polyether, polyamide, polyvinyl chloride, a copolymer of vinyl chloride and vinyl acetate and polyvinylidene chloride; thermosetting resins such as a phenolic resin, a melamine resin, an epoxy resin, an unsaturated polyester resin and an alkyd resin; and rubbers such as EPDM, SBR, NBR, butyl rubber, isoprene rubber and chlorosulfonated polyethylene rubber.

The present invention provides a novel anti-microorganism agent composed of the composite metal hydroxide of the formula (1) which is a solid solution of copper ion and/or zinc ion in calcium hydroxide and/or magnesium hydroxide. This anti-microorganism agent exhibits anti-microorganism activity by releasing a proper amount of copper ion and/or zinc ion, and improves the heat resistance and weatherability of resins and rubbers without impairing the properties thereof when contained in the resins and rubbers.

The present invention also provides a novel anti-microorganism agent composed of the composite metal oxide of the formula (2) which is a solid solution of cupric oxide and/or zinc oxide in calcium oxide and/or magnesium oxide. This anti-microorganism agent excellent anti-microorganism activity over sparingly soluble cupric oxide and zinc oxide by releasing copper ion and/or zinc ion at a solubility close to the solubility of calcium oxide or magnesium oxide in water. Further, this anti-microorganism agent is excellent in dispersibility in resin, rubbers and coating compositions, and characteristically improves these resins, etc., in heat resistance and weatherability without impairing the properties thereof.

The present invention will be explained further in detail by reference to Examples.

EXAMPLE 1

200 Milliliters of deionized water having a temperature of 40° C. was placed in a stainless steel reaction vessel having an internal volume of 1 liter, and 500 ml of a Ca(OH)$_2$ slurry containing 2.0 mol/l of Ca(OH)$_2$ and 50 ml of a zinc nitrate aqueous solution containing 1.0 mol/l of zinc nitrate were added to the deionized water with stirring while taking about 2 minutes to finish the addition of the total amount of the Ca(OH)$_2$ slurry and the zinc nitrate aqueous solution. Then, the resultant mixture was further allowed to react for 10 minutes with stirring to give a white slurry. The slurry was filtered and washed with water, and the resultant solid was dried and milled.

The above-obtained product showed the same powder X-ray diffraction pattern as that of Ca(OH)$_2$ except that the diffraction pattern slightly shifted toward a higher angle side. The product was measured for a chemical composition by a chelate titration method. The product was dispersed with supersonic wave and then measured for a secondary particle diameter by a microtrack method using laser beam. The anti-microorganism activity of the product was tested as follows. A solution having a predetermined concentration of test microorganisms was applied to agar media and cultivated in the presence of the product in a variety of concentrations. A concentration at which the growth of the microorganisms was inhibited was taken as a minimum concentration for growth inhibition. Table 1 shows the results.

EXAMPLE 2

300 Milliliters of deionized water having a temperature of 40° C. was placed in a stainless steel reaction vessel having an internal volume of 2 liters, and 500 ml of a mixed aqueous solution containing 1.1 mol/l of calcium chloride and 0.9 mol/l of zinc nitrate and 500 ml of a sodium hydroxide aqueous solution containing 4 mol/l of sodium hydroxide were simultaneously added with stirring while taking about 5 minutes to finish the addition of the total amount of these. The reaction mixture was filtered and washed with water, and the remaining solid was dried and milled to give a powder.

The above-obtained powder showed the same X-ray diffraction pattern as that of Ca(OH)$_2$ except that the diffraction pattern slightly shifted toward a higher angle side and also showed a diffraction pattern of Ca[Zn(OH)$_3$]$_2$.2H$_2$O. The powder was measured in the same manner as in Example 1 , and Table 1 shows the results.

EXAMPLE 3

500 Milliliters of a mixed aqueous solution containing 1.96 mol/l of calcium chloride and 0.04 mol/l of zinc chloride and 500 ml of a potassium hydroxide aqueous solution containing 4 mol/l of potassium hydroxide were treated in the same manner as in Example 2 to give a powder. The powder showed the same X-ray diffraction pattern as that of Ca(OH)$_2$ except that the diffraction pattern slightly shifted toward a higher angle side. The powder was measured in the same manner as in Example 1. Table 1 shows the results.

EXAMPLE 4

500 Milliliters of a slurry containing 2 mol/l of Ca(OH)$_2$ and 150 ml of a cupric chloride aqueous solution containing 1.0 mol/l of cupric chloride were treated in the same manner as in Example 1 to give a powder. The powder showed the same X-ray diffraction pattern as that of Ca(OH)$_2$ except that the diffraction pattern slightly shifted toward a higher angle side. The powder was measured in the same manner as in Example 1. Table 1 shows the results.

EXAMPLE 5

Deionized water having a temperature of 30° C. was placed in a reaction vessel having an internal volume of 2 liters, and while the deionized was stirred, 500 ml of a Ca(OH)$_2$ slurry containing 2 mol/l of Ca(OH)$_2$ and 550 ml of a cupric chloride aqueous solution containing 1.0 mol/l of cupric chloride were added almost simultaneously over about 5 minutes. Further, the resultant mixture was allowed to react for about 10 minutes with stirring. Then, the reaction mixture was treated in the same manner as in Example 1 to give a powder. The powder showed the same X-ray diffraction pattern as that of Ca(OH)$_2$ except that the diffraction pattern slightly shifted toward a higher angle side and also showed a diffraction pattern of basic copper chloride. The powder was measured in the same manner as in Example 1, and Table 1 shows the results.

EXAMPLE 6

600 Milliliters of ammonia water containing 2 mol/l of ammonia was added to 5 liters of a magnesium chloride aqueous solution containing 3.0 mol/l of magnesium chloride, and the resultant mixture was allowed to react for 5 days while its temperature was kept at 40° C. Then, 20 ml of a cupric chloride aqueous solution containing 1.0 mol/l of cupric chloride was added to the resultant reaction mixture, and the resultant mixture was allowed to react for about 30 minutes. The reaction mixture was dehydrated, washed with water and dehydrated to give a cake-like product. The cake-like product was added to 500 ml of a sodium hydroxide aqueous solution containing 5 mol/l of sodium hydroxide while the sodium hydroxide aqueous solution was stirred at 90° C., and the resultant mixture was allowed to react for about 20 minutes. The reaction product was filtered, washed with water, dried and sieved to give a powder. The powder was a crystal having the form of fibers, and the powder showed the same X-ray diffraction pattern as that of Mg(OH)$_2$ except that the diffraction pattern slightly shifted toward a lower angle side. The powder was measured in the same manner as in Example 1 . Table 1 shows the results.

EXAMPLE 7

500 milliliters of a mixed aqueous solution containing 0.2 mol/l of magnesium chloride and 0.12 mol/l of zinc nitrate and 500 ml of a Ca(OH)$_2$ slurry containing 2.0 mol/l of Ca(OH)$_2$ were allowed to react and treated in the same manner as in Example 1 to give a powder. The powder showed the same X-ray diffraction pattern as that of Mg(OH)$_2$ except that the diffraction pattern slightly shifted toward a lower angle side. The powder was measured in the same manner as in Example 1. Table 1 shows the results.

COMPARATIVE EXAMPLE 1

500 milliliters of a mixed aqueous solution containing 0.2 mol/l of calcium chloride and 1.8 mol/l of zinc nitrate and 500 ml of a sodium hydroxide aqueous solution containing 4 mol/l of sodium hydroxide were allowed to react and treated in the same manner as in Example 2 to give a powder. The powder showed only the X-ray diffraction pattern of ZnO. The powder was measured in the same manner as in Example 1. Table 1 shows the results.

COMPARATIVE EXAMPLES 2 AND 3

Commercially available anti-microorganism agents, cuprous oxide (Comparative Example 2) and copper-supported borosilicate glass (Comparative Example 3), were measured in the same manner as in Example 1. Table 1 shows the results.

TABLE 1

| Anti-microorganism agent | | Average secondary particle diameter ($\mu$m) | Anti-microorganism activity (%)*1 | |
|---|---|---|---|---|
| | | | *Escherichia coli* | Yellow Staphylococcus |
| Ex. 1 | $Ca_{0.95}Zn_{0.05}(OH)_2$ | 0.96 | 0.125 | 0.1 |
| Ex. 2 | $Ca_{0.55}Zn_{0.45}(OH)_2 \cdot mH_2O$ | 1.28 | 0.25 | 0.1 |
| Ex. 3 | $Ca_{0.98}Cu_{0.02}(OH)_2$ | 0.80 | 0.125 | 0.1 |
| Ex. 4 | $Ca_{0.85}Cu_{0.15}(OH)_2$ | 0.72 | 0.05 | 0.05 |
| Ex. 5 | $Ca_{0.55}Cu_{0.45}(OH)_{2-w}Cl_w \cdot mH_2O$ | 1.91 | 0.25 | 0.1 |
| Ex. 6 | $Mg_{0.97}Cu_{0.03}(OH)_2$ | 0.76 | 0.25 | 0.125 |
| Ex. 7 | $Ca_{0.84}Mg_{0.10}Zn_{0.06}(OH)_2$ | 0.43 | 0.25 | 0.125 |
| CEx. 1 | $Ca_{0.1}Zn_{0.9}O_w(OH)_{2-2w} \cdot H_2O$ | 5.14 | 1.0 or more | 1.0 or more |
| CEx. 2 | $Cu_2O$ | 1.69 | 1.0 or more | 1.0 or more |
| CEx. 3 | Borosilicate glass*1 | 25.3 | 1.0 | 0.5 |

Ex. = Example,
CEx. = Comparative Example
*1 = Minimum concentration for growth inhibition
*2 = copper-containing anti-microorganism agent (trade (name, Ionpure, supplied by Ishizuka Glass Co.)

TABLE 2

| Anti-mold agent | | Heat stability (minute) | Evaluation on anti-mold activity (days of culturing) | | | |
|---|---|---|---|---|---|---|
| | | | 7 | 14 | 21 | 28 |
| Ex. 8 | $Ca_{0.95}Zn_{0.05}(OH)_2$ | 70 | 0 | 0 | 0 | 0 |
| Ex. 9 | $Ca_{0.85}Cu_{0.15}(OH)_2$ | 60 | 0 | 0 | 0 | 0 |
| Ex. 10 | $Mg_{0.97}Cu_{0.03}(OH)_2$ | 60 | 0 | 0 | 0 | 1 |
| Ex. 11 | $Ca_{0.84}Mg_{0.10}Zn_{0.06}(OH)_2$ | 70 | 0 | 0 | 0 | 1 |
| CEx. 14 | nil | 40 | 3 | 4 | 4 | 4 |

Ex. = Example,
CEx. = Comparative Example
Evaluation on anti-mold activity:
0: No growth of mold was observed.
1: Slight growth of mold was observed.
2: A little growth of mold was observed.
3. Clear growth of mold was observed.
4. Thick growth of mold was observed.

EXAMPLES 8-11

In each Example, soft vinyl chloride sheets were prepared as follows. 100 Parts by weight of polyvinyl chloride (average polymerization degree 1,300), 50 parts by weight of dioctyl phthalate, 2 parts by weight of a Ba/Zn composite heat stabilizer (trade name "KV62B-4", supplied by Kyodo Pharmaceutical Co., Ltd.), 2 parts by weight of epoxidized soybean oil, and 1 part by weight of an anti-mold agent (shown in Table 2) were homogeneously mixed, and the mixture was melt-kneaded with a roll mill at 170° C. for 3 minutes. Then, the mixture was press-molded with a press-molding machine at 170° C. for 2 minutes under a pressure of 200 kg/cm$^2$ into sheets having a thickness of 1 mm. In addition, the anti-mold agents used in Examples 8, 9, 10 and 11 corresponded to the powders prepared in Examples 1, 4, 6 and 7 in this order.

Penicillium was sprayed onto one of the above sheets, and the state of growth of the penicillium was observed. On the other hand, one of the sheets was placed in an oven at 190° C., and measured for a time until it turned black. Vinyl chloride turns black when it thermally deteriorates. Therefore, standing intact for a longer time before a sheet turns black means having superior heat stability. Table 2 shows the results.

COMPARATIVE EXAMPLE 4

Example 8 was repeated except that no anti-mold agent was incorporated.

EXAMPLE 12

2 Liters of a magnesium nitrate/cupric nitrate mixed aqueous solution ($Mg^{2+}=1.05$ mol/l, $Cu^{2+}=0.05$ mol/l) was placed in a stainless steel cylindrical reactor having an internal volume of 5 liters. While the mixed aqueous solution was stirred, 2 liters of a $Ca(OH)_2$ aqueous solution containing 1.0 mol/l of $Ca(OH)_2$ and having a temperature of 25° C. was added, and the resultant mixture was allowed to react. The resultant reaction product was aged under heat at 100° C. for 1 hour, filtered, washed with water, dried and milled. The resultant product was calcined in a silicon carbide furnace at 450° C. for 1 hour.

The composite metal oxide had a chemical composition of $Mg_{0.95}Cu_{0.05}O$. The composite metal oxide did not show any X-ray diffraction pattern of cuprio oxide, but showed an X-ray diffraction pattern corresponding to that of magnesium oxide. That is, it was shown that a solid solution of cupric oxide in magnesium oxide was formed. The chemical composition of the composite metal oxide was determined by a chelate titration method. The product was dispersed with a supersonic wave method using ethanol as a solvent and then measured for a secondary particle diameter by a microtrack method, The anti-microorganism activity of the composite metal oxide was tested in the same manner as in Example 1. Table 3 shows the results.

EXAMPLE 13

2 Liters of a magnesium nitrate/zinc nitrate mixed aqueous solution ($MG^{2+}=1.1$ mol/l, $Zn^{2+}=0.02$ mol/l) was placed in a stainless steel cylindrical reactor having an internal volume of 5 liters. While the mixed aqueous solution was stirred, 2 liters of a Ca(OH)$_2$ aqueous solution containing 1.0 mol/l of Ca(OH)$_2$ and having a temperature of 20° C. was added, and the resultant mixture was allowed to react. The resultant reaction product was aged under heat at 120° C. for 2 hours, filtered, washed with water, dried and milled. The resultant product was calcined in a silicon carbide furnace at 500° C. for 1 hour.

The resultant composite metal oxide had a chemical composition of Mg$_{0.98}$Zn$_{0.02}$O. The composite metal oxide showed only an X-ray diffraction pattern corresponding to that of magnesium oxide. That is, it was shown that a solid solution of zinc oxide in magnesium oxide was formed. The composite metal oxide was measured in the same manner as in Example 12. Table 3 shows the results.

EXAMPLE 14

2 Liters of a calcium nitrate/cupric nitrate mixed aqueous solution (Ca$^{2+}$ = 0.85 mol/l, Cu$^{2+}$ = 0.15 mol/l, 30° C.) and 2 liters of an NaOH aqueous solution containing 2.0 mol/l of NaOH and having a temperature of 30° C. were continuously charged into a reactor having an internal volume of 5 liters and containing 500 ml of water at a rate of 50 ml/minute each by means of quantity measuring pumps to allow them to react. The resultant reaction product was filtered, washed with water, dehydrated, dried and milled. The resultant product was calcined in a silicon carbide furnace at 550° C. for 1 hour.

The resultant composite metal oxide had a chemical composition of Ca$_{0.82}$Cu$_{0.18}$O. The composite metal oxide showed only an X-ray diffraction pattern corresponding to that of CaO. That is, it was shown that a solid solution of CuO in CaO was formed. The composite metal oxide was measured in the same manner as in Example 12. Table 3 shows the results.

EXAMPLE 15

4 Liters of a slurry (20° C.) containing 1.0 mol/l of Ca(OH)$_2$ synthesized from NaOH and Ca(NO$_3$)$_2$ was placed in a reaction vessel having an internal volume of 5 liters. While the slurry was stirred, 240 ml of a zinc nitrate aqueous solution (20° C.) containing 1.0 mol/l of zinc nitrate was added to allow them to react. The resultant reaction product was filtered, washed with water, dehydrated, dried and milled. The resultant product was calcined in a silicon carbide furnace at 600° C. for 1 hour.

The resultant composite metal oxide had a chemical composition of Ca$_{0.94}$Zn$_{0.06}$O. The composite metal oxide showed only an X-ray diffraction pattern corresponding to that of CaO. That is, it was shown that a solid solution of ZnO in CaO was formed. The composite metal oxide was measured in the same manner as in Example 12. Table 3 shows the results.

EXAMPLE 16

2 Liters of a slurry (20° C.) containing 1.0 mol/l of synthetic Ca(OH)$_2$ was placed in a reaction vessel having an internal volume of 5 liters. While the slurry was stirred, 2 liters of a magnesium nitrate/cupric nitrate mixed aqueous solution (Mg$^{2+}$ = 0.08 mol/l, Cu$^{2+}$ = 0.10 mol/l, 20° C.) was added to allow the resultant mixture to react. The resultant reaction product was filtered, washed with water, dried and milled. Then, the resultant product was calcined in a silicon carbide furnace at 600° C. for 1 hour.

The resultant composite metal oxide had a chemical composition of Ca$_{0.82}$Mg$_{0.08}$Cu$_{0.10}$O. The composite metal oxide showed only an X-ray diffraction pattern corresponding to that of CaO. That is, it was shown that a solid solution of MgO and CuO in CaO was formed. The composite metal oxide was measured in the same manner as in Example 12. Table 3 shows the results.

EXAMPLE 17

31 Grams of a magnesium oxide powder was added to 5 liters of a magnesium chloride aqueous solution containing 3.0 mol/l of magnesium chloride with stirring, and the resultant mixture was kept at 40° C. for 7 dyas to allow it to react. Then, 35 ml of a zinc chloride aqueous solution containing 1.0 mol/l of zinc chloride was added, and the resultant mixture was allowed to react for about 30 minutes. The resultant reaction product was filtered and washed with water to give a cake-like product. The cake-like product was added to 500 ml of a sodium hydroxide aqueous solution containing 5 mol/l of sodium hydroxide and having a temperature of 90° C. with stirring, and the resultant mixture was allowed to react for about 20 minutes. The reaction product was filtered, washed with water, dried and sieved. The resultant product was calcined in air atmosphere in an electric oven at 500° C. for 1 hour.

The so-obtained composite metal oxide had a chemical composition of Mg$_{0.96}$Zn$_{0.04}$O. This composite metal oxide was observed through a scanning electron microscope to show a fibrous form having a diameter of approximately 0.2 to 0.3 μm and a length of approximately 20 to 60 μm. This composite metal oxide showed nearly the same powder X-ray diffraction pattern as that of magnesium oxide, and no zinc oxide was detected. The composite metal oxide was measured in the same manner as in Example 12. Table 3 shows the results.

COMPARATIVE EXAMPLE 5

2 Liters of a slurry (20° C.) containing 1.0 mol/l of synthetic Ca(OH)$_2$ was placed in a reaction vessel having an internal volume of 5 liters. While the slurry was stirred, 2 liters of a cupric nitrate aqueous solution (20° C.) containing 0.6 mol/l of cupric nitrate was added to the slurry, and the resultant mixture was allowed to react. The reaction product was filtered, washed with water, dried and milled. The resultant product was calcined in a silicon carbide furnace at 600° C. for 1 hour.

The resultant product had a chemical composition of Ca$_{0.4}$Cu$_{0.6}$O. The product showed two X-ray diffraction patterns corresponding to those of CaO and CuO. That is, it was shown that CuO which was not forming a solid solution with CaO was present. The product was measured in the same manner as in Example 12. Table 3 shows the results.

COMPARATIVE EXAMPLES 6 AND 7

Commercially available CuO as first grade reagent (Comparative Example 6) and ZnO (French method, special grade, Comparative Example 7) were tested in the same manner as in Example 12. Table 3 shows the results.

TABLE 3

| | Average secondary particle diameter (μm) | Anti-microorganism activity (%)*1 | |
|---|---|---|---|
| | | *Escherichia coli* | Yellow Staphylococcus |
| Ex. 12 | 1.10 | 0.05 | 0.05 |
| Ex. 13 | 0.34 | 0.125 | 0.1 |
| Ex. 14 | 0.72 | 0.025 | 0.025 |
| Ex. 15 | 1.20 | 0.125 | 0.1 |
| Ex. 16 | 0.87 | 0.05 | 0.05 |
| Ex. 17 | diameter 0.2–0.3 length 20–60 | | |
| CEx. 5 | 3.40 | 1.0 or more | 1.0 or more |
| CEx. 6 | — | 1.0 or more | 1.0 or more |
| CEx. 7 | 0.50 | 1.0 or more | 1.0 or more |

Ex. = Example,
CEx. = Comparative Example
*1: Minimum concentration for growth inhibition

EXAMPLES 18 AND 19, AND COMPARATIVE EXAMPLES 8 AND 9

In each Example, soft vinyl chloride sheets were prepared as follows. 100 Parts by weight of polyvinyl chloride (average polymerization degree 1,300), 50 parts by weight of dioctyl phthalate, 2 parts by weight of a Ba/Zn composite heat stabilizer (trade name "KV62B-4", supplied by Kyodo Pharmaceutical Co., Ltd.), 2 parts by weight of epoxidized soybean oil, and 1 part by weight of an anti-mold agent (shown in Table 4) were homogeneously mixed, and the mixture was melt-kneaded with a roll mill at 170° C. for 3 minutes. Then, the mixture was press-molded with a press-molding machine at 170° C. for 2 minutes under a pressure of 200 kg/cm² into sheets having a thickness of 1 mm. In addition, the anti-mold agents used in Examples 18 and 19 corresponded to the anti-microorganism agents prepared in Examples 12 and 15. Comparative Examples 8 and 9 used CuO and ZnO described in Comparative Examples 6 and 7.

Penicillium was sprayed onto one of the above sheets, and the state of growth of the penicillium was observed. On the other hand, one of the sheets was placed in an oven at 190° C., and measured for a time until it turned black. Vinyl chloride turns black when it thermally deteriorates. Therefore, standing intact for a longer time before a sheet turns black means having superior heat stability. Table 4 shows the results.

TABLE 4

| Anti-mold agent | Heat stability (minute) | Evaluation on anti-mold activity (days of culturing) | | | |
|---|---|---|---|---|---|
| | | 7 | 14 | 21 | 28 |
| Ex. 18 | $Mg_{0.95}Cu_{0.05}O$ | 70 | 0 | 0 | 0 | 0 |
| Ex. 19 | $Ca_{0.94}Zn_{0.06}O$ | 80 | 0 | 0 | 0 | 1 |
| CEx. 8 | CuO | 5 | 2 | 3 | 4 | 4 |
| CEx. 9 | ZnO | 10 | 3 | 4 | 4 | 4 |

Ex. = Example,
CEx. = Comparative Example
Evaluation on anti-mold activity:
0: No growth of mold was observed.
1: Slight growth of mold was observed.
2: A little growth of mold was observed.
3. Clear growth of mold was observed.
4. Thick growth of mold was observed.

What is claimed is:

1. An anti-microorganism agent composed of at least one member selected from the group consisting of a composite metal hydroxide which is a solid solution of the formula (1), $$(M_1^{2+})_{1-x}(M_2^{2+})_x(OH)_2 \tag{1}$$

wherein $M_1^{2+}$ is at least one member selected from the group consisting of $Mg^{2+}$ and $Ca^{2+}$, $M_2^{2+}$ is at least one member selected from the group consisting of $Cu^{2+}$ and $Zn^{2+}$, and x is defined by $0.001 \leq x \leq 0.4$, and a composite metal oxide which is a solid solution of the formula (2), $$(M_1^{2+})_{1-y}(M_2^{2+})_y O \tag{2}$$

wherein $M_1^{2+}$ is at least one member selected from the group consisting of $Mg^{2+}$ and $Ca^{2+}$, $M_2^{2+}$ is at least one member selected from the group consisting of $Cu^{2+}$ and $Zn^{2+}$, and y is defined by $0.001 \leq y \leq 0.5$.

2. An anti-microorganism agent according to claim 1, wherein y in the formula (2) is defined by $0.005 \leq y \leq 0.4$.

3. An anti-microorganism resin or rubber composition containing 100 parts by weight of a resin or rubber and 0.001 to 50 parts by weight of the anti-micoroorganism agent as recited in claim 1.

* * * * *